United States Patent
Knopf et al.

(10) Patent No.: US 12,239,078 B2
(45) Date of Patent: Mar. 4, 2025

(54) RIPENESS DETECTION SYSTEM USING HUE COLOR SPACE AND PEAK FINDING

(71) Applicant: APPHARVEST TECHNOLOGY, INC., Morehead, KY (US)

(72) Inventors: Ryan R. Knopf, Morehead, KY (US); Joshua Aaron Lessing, Morehead, KY (US)

(73) Assignee: ZORDI, INC., Boston, MA (US)

(*) Notice: Subject to any disclaimer, the term of this patent is extended or adjusted under 35 U.S.C. 154(b) by 378 days.

(21) Appl. No.: 17/430,771

(22) PCT Filed: Feb. 14, 2020

(86) PCT No.: PCT/US2020/018395
§ 371 (c)(1),
(2) Date: Aug. 13, 2021

(87) PCT Pub. No.: WO2020/168264
PCT Pub. Date: Aug. 20, 2020

(65) Prior Publication Data
US 2022/0164989 A1    May 26, 2022

Related U.S. Application Data (60) Provisional application No. 62/806,492, filed on Feb. 15, 2019.

(51) Int. Cl.
*G06T 7/90* (2017.01)
*A01H 6/54* (2018.01)
(Continued)

(52) U.S. Cl.
CPC ............. *A01H 6/542* (2018.05); *G01N 21/95* (2013.01); *G06T 7/44* (2017.01); *G06T 7/90* (2017.01);
(Continued)

(58) Field of Classification Search
None
See application file for complete search history.

(56) References Cited

U.S. PATENT DOCUMENTS 6,901,163 B1 * 5/2005 Pearce ..................... G01J 3/50
  382/218
9,468,152 B1   10/2016 Jens et al.
(Continued)

FOREIGN PATENT DOCUMENTS

| CN | 106067181 A | * 11/2016 |
| CN | 108122238 A |   6/2018 |
| CN | 108279238   |   7/2018 |
| CN | 108279238 A | * 7/2018 |

(Continued)

OTHER PUBLICATIONS

Office Action dated Nov. 17, 2022 for Saudi Arabia Application No. 521430066, 14 pages.
(Continued)

*Primary Examiner* — Bernard Krasnic
(74) *Attorney, Agent, or Firm* — Benesch Friedlander Coplan & Aronoff LLP (57) ABSTRACT

A method for estimating ripeness of produce includes illuminating the produce with light, measuring intensities of the light reflected from the produce at different frequencies, and determining a degree of ripeness of the produce from the relative intensities of the light reflected from the produce at the different frequencies.

26 Claims, 10 Drawing Sheets

(51) Int. Cl.
*G01N 21/95* (2006.01)
*G06T 7/44* (2017.01)
*G06V 20/68* (2022.01)

(52) U.S. Cl.
CPC .......... *G06V 20/68* (2022.01); *G06F 2218/14* (2023.01); *G06T 2207/10024* (2013.01)

(56) References Cited

U.S. PATENT DOCUMENTS

2008/0101657 A1     5/2008   Durkin et al.
2011/0137456 A1     6/2011   Koselka et al.
2016/0187199 A1*   6/2016   Brunk .................. G01J 3/0208
                                                                               348/89

FOREIGN PATENT DOCUMENTS

| CN | 108617264 A | | 10/2018 |
|---|---|---|---|
| KR | 20190015656 A | * | 2/2019 |
| WO | 2006135267 A2 | | 12/2006 |
| WO | 2015121809 A1 | | 8/2015 |

OTHER PUBLICATIONS

Office Action dated Jun. 17, 2023 for Australia application No. 2020221400, 5 pages.
Office Action issued in related Israeli patent application No. 285591, dated Dec. 27, 2023.
Liévin, M., et al., "Nonlinear Color Space and Spatiotemporal MRF for Hierarchical Segmentation of Face Features in Video", IEEE Transactions on Image Processing, vol. 13, No. 1, Jan. 2004.

* cited by examiner

RIPENESS DETECTION SYSTEM USING HUE COLOR SPACE AND PEAK FINDING

TECHNICAL FIELD

Aspects and embodiments disclosed herein relate to machine imaging of agricultural products to determine degree of ripeness of same.

BACKGROUND

To direct automated multi-degree-of-freedom systems (robotic systems) to interact with living plants for harvest, pruning, trellising, or various forms of analysis, it may be desirable for the robotic system to be able to determine a degree of ripeness of agricultural produce or fruits of the living plants. A determination of the degree of ripeness of the agricultural produce or fruits may inform a decision regarding whether the agricultural produce or fruits are of sufficient ripeness for harvest.

SUMMARY

In accordance with one aspect, there is provided a method for estimating ripeness of produce. The method comprises illuminating the produce with light, measuring intensities of the light reflected from the produce at different frequencies, and determining a degree of ripeness of the produce from the relative intensities of the light reflected from the produce at the different frequencies.

In some embodiments, the method further comprises selecting a cropped region of an image of the produce which is a same size as an individual target item of produce for which ripeness is to be calculated.

In some embodiments, the cropped region of the image is selected such that greater than 50% of pixels in the cropped region of the image are included in an image of the individual target item of produce.

In some embodiments, the method further comprises converting the cropped region of the image to a hue, saturation, and value (HSV) color representation.

In some embodiments, the method further comprises computing a histogram of pixel population of the cropped region of the image by hue and saturation.

In some embodiments, the method further comprises identifying a peak in the hue histogram.

In some embodiments, the method further comprises determining the degree of ripeness of the individual target item of produce from a location of the peak in the hue histogram.

In some embodiments, the method further comprises calibrating a hue histogram peak location versus produce ripeness scale for different varieties of produce.

In some embodiments, the method is utilized to estimate ripeness of produce which exhibits a change in concentration of one or more of $\beta$-carotene, lutein, lycopene, or other carotenoids as the produce ripens.

In some embodiments, the method is utilized to estimate ripeness of produce selected from the group consisting of tomatoes, peppers, and cucumbers.

In some embodiments, the method further comprises providing an indication of whether the produce is sufficiently ripe for harvesting based on the determination of the degree of ripeness of the produce.

In some embodiments, the method further comprises communicating the indication of whether the produce is sufficiently ripe for harvesting to a robotic system configured to harvest the produce.

In some embodiments, the method further comprises harvesting produce with the robotic system responsive to the produce being sufficiently ripe for harvesting.

In accordance with another aspect, there is provided a method for estimating ripeness of produce in an indoor agricultural environment having an ambient light power spectrum that differs from a power spectrum of natural outdoor light. The method comprises illuminating the produce with light in a bandwidth that is reflected from the produce to a degree that varies with ripeness of the produce, measuring an intensity of the light reflected from the produce, and determining a degree of ripeness of the produce from the intensity of the light reflected from the produce.

In some embodiments, illuminating the produce includes illuminating the produce with green light.

In some embodiments, illuminating the produce includes illuminating the produce with light in a frequency band of from 520 nm to 560 nm.

In accordance with another aspect, there is provided a system for estimating ripeness of produce. The system comprises an image sensor configured to measure intensities of light reflected from the produce at different frequencies, and a processor configured to determining a degree of ripeness of the produce from relative intensities of the light reflected from the produce at the different frequencies.

In some embodiments, the processor is further configured to select a cropped region of an image of the produce which is a same size as an individual target item of produce for which ripeness is to be calculated.

In some embodiments, the processor is further configured to select the cropped region of the image such that greater than 50% of pixels in the cropped region of the image are included in an image of the individual target item of produce.

In some embodiments, the processor is further configured to convert the cropped region of the image to a hue, saturation, and value (HSV) color representation.

In some embodiments, the processor is further configured to compute a histogram of pixel population of the cropped region of the image by hue and saturation.

In some embodiments, the processor is further configured to identify a peak in the hue histogram.

In some embodiments, the processor is further configured to determine the degree of ripeness of the individual target item of produce from a location of the peak in the hue histogram.

In some embodiments, the system further comprises a robotic harvester in communication with the processor and configured to harvest the individual target item of produce.

In some embodiments, the processor is further configured to provide an indication of whether the produce is sufficiently ripe for harvesting responsive to determining the degree of ripeness of the produce.

In some embodiments, the processor is further configured to communicate the indication of whether the produce is sufficiently ripe for harvesting to a robotic system configured to harvest the produce.

In some embodiments, the system further comprises the robotic system configured to harvest the produce.

In accordance with another aspect, there is provided a robotic harvester configured to harvest items of agricultural produce identified as sufficiently ripe for harvesting by a system comprising an image sensor configured to measure intensities of light reflected from the produce at different frequencies and a processor configured to determining a degree of ripeness of the produce from relative intensities of the light reflected from the produce at the different frequencies.

In accordance with another aspect, there is provided a system for estimating ripeness of produce in an indoor agricultural environment having an ambient light power spectrum that differs from a power spectrum of natural outdoor light. The system comprises a projector configured to illuminate the produce with light in a bandwidth that is reflected from the produce to a degree that varies with ripeness of the produce, a light intensity meter configured to measure an intensity of the light reflected from the produce, and a processor configured to determine a degree of ripeness of the produce from the intensity of the light reflected from the produce.

In some embodiments, the projector is configured to output green light.

In some embodiments, the projector is configured to output light in a frequency band of from 520 nm to 560 nm.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Aspects and implementations disclosed herein are not limited to the details of construction and the arrangement of components set forth in the following description or illustrated in the drawings. Aspects and implementations disclosed herein are capable of being practiced or of being carried out in various ways.

Humans may utilize various cues to determine whether a growing agricultural product such as fruits, berries, or vegetables, referred to collectively herein as "produce," are ripe and ready for harvesting. A human may, for example, examine the color, firmness, or in some instances, smell of the produce to determine its degree of ripeness. Sensory systems of agricultural robots currently are often less capable of utilizing the same cues humans may use to determine a degree of ripeness of growing agricultural produce. It would be desirable to provide an agricultural robot with the ability to determine the degree of ripeness of agricultural produce so that the robot may automatically determine whether the produce is ripe for harvest and can initiate harvest without the need for human intervention, thus increasing the efficiency of operation of the agricultural robot.

Aspects and embodiments disclosed herein include systems and methods for determining a degree of ripeness of agricultural produce by measuring light reflected from the produce. The produce may be illuminated with a specific wavelength of light or with a broad-band illumination source, for example, white light or ambient light. The intensity of reflected light at a particular wavelength or a particular wavelength that is reflected to a higher degree than other wavelengths may provide an indication of the ripeness of the produce.

Figure 1:
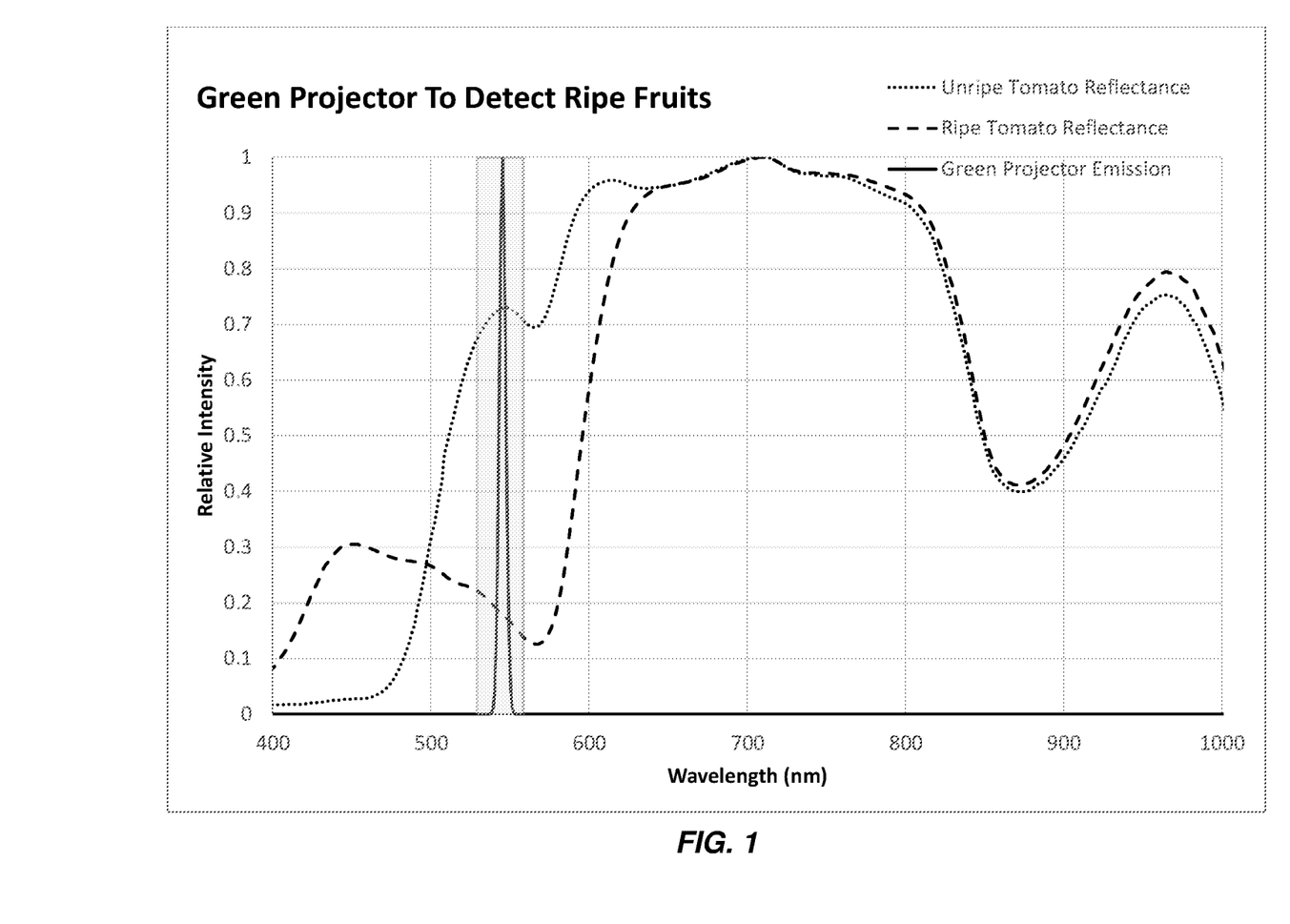
FIG. 1 illustrates a difference in reflectivity of green light for certain unripe and ripe agricultural produce.

Determining Ripeness Based on Intensity of Selected Wavelengths of Reflected Light As shown in FIG. 1, fruits and vegetables, in particular those that gain their pigmentation from bio-synthetic production of β-carotene (orange fruits), lutein (yellow fruits), lycopene (red fruits), or other carotenoids as they ripen absorb light in the 520-560 nm band by an amount that is strongly correlated with the degree of ripeness. Thus, standard image processing techniques to measure the contrast ratio of a projected pattern of light in the 520-560 nm band against the rest of the scene can be directly used as a proportional measurement of fruit ripeness under controlled ambient lighting conditions.

Figure 2:
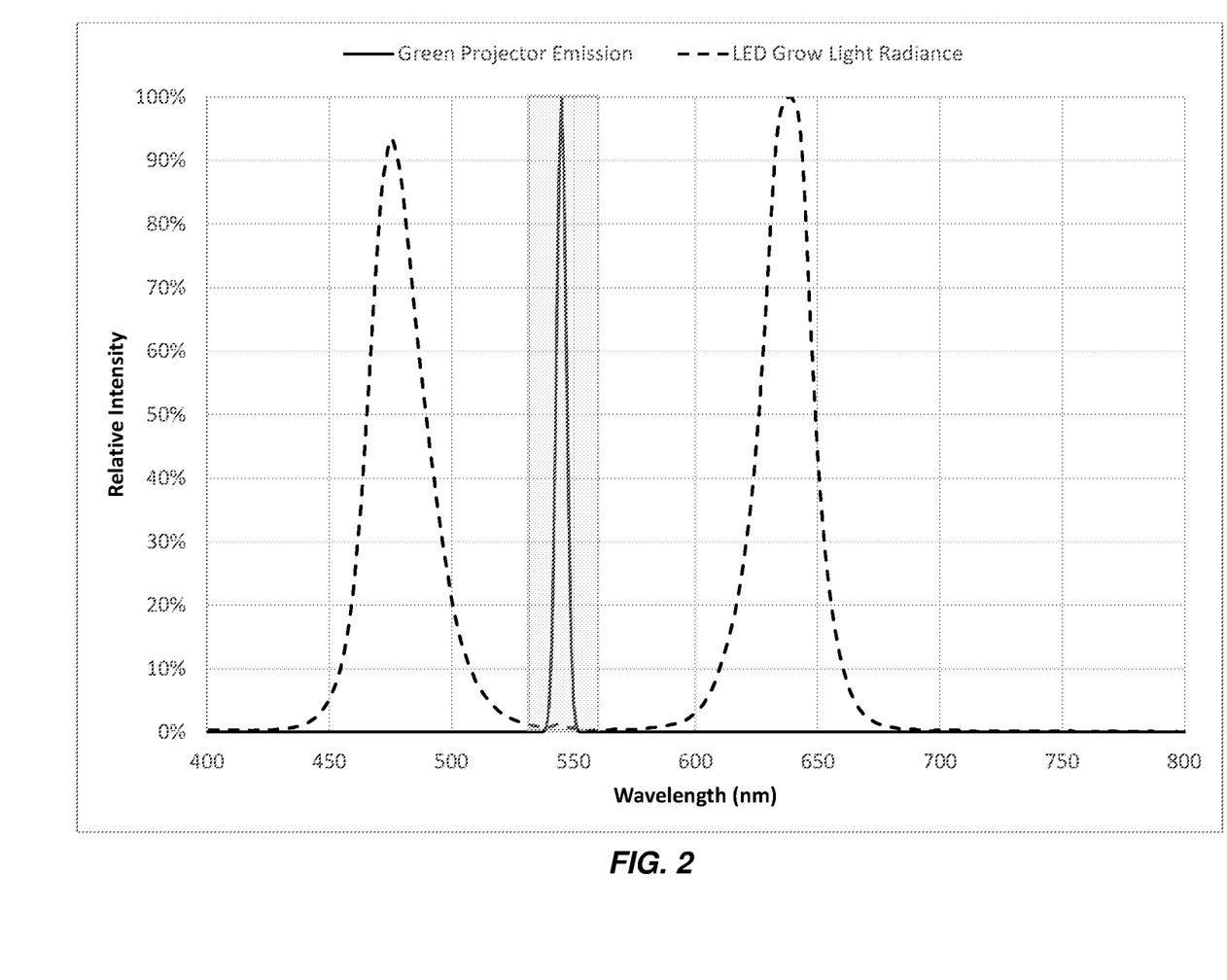
FIG. 2 illustrates the relative intensity of light in a green band width versus red and blue wavelengths of light used for illumination in some greenhouses.

This ripeness detection feature might be most useful when paired with a red-blue artificial ambient lighting environment which is used in some greenhouses (See FIG. 2), but it is also contemplated that it may be used under a natural lighting environment as well.

Embodiment of Ripeness Detection Using Hue Color Space and Peak Finding

Figure 5:
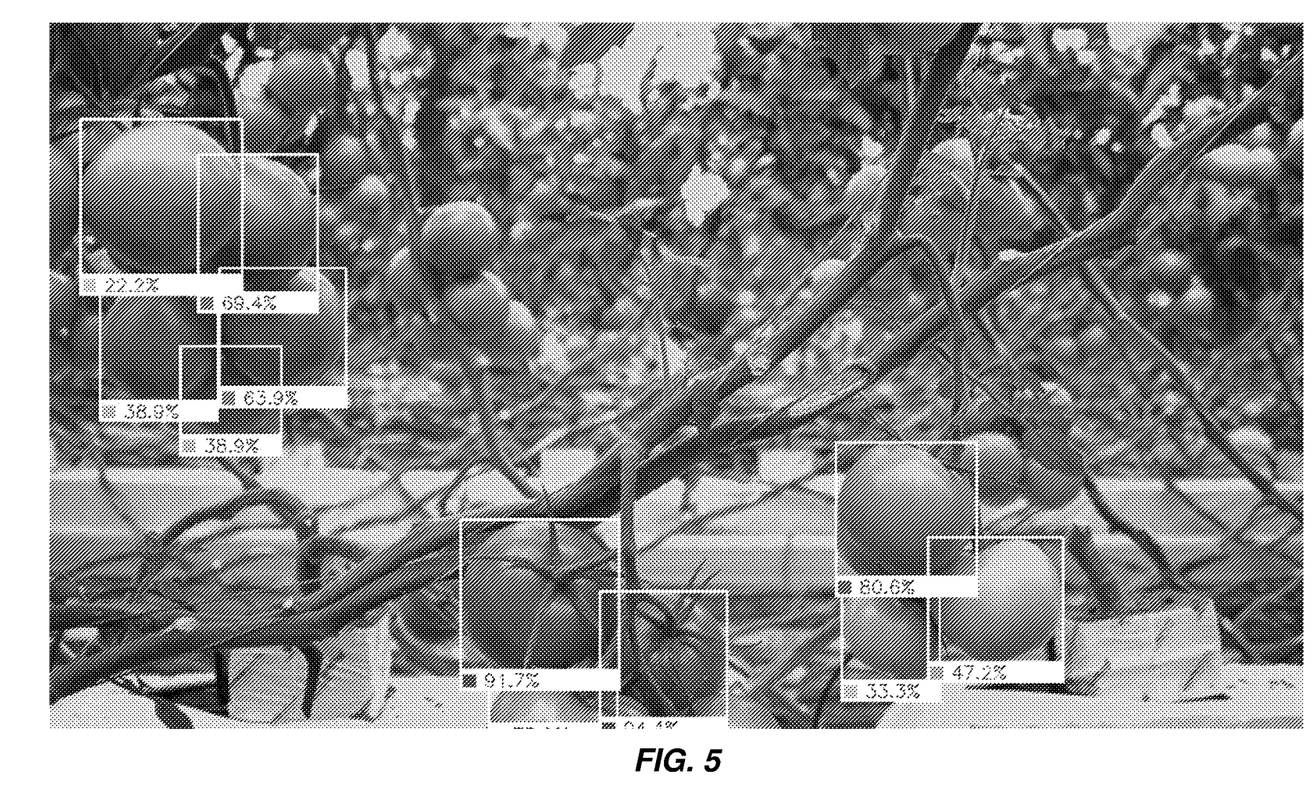
FIG. 5 illustrates a number of tomatoes identified by an agricultural robot and ripeness percentages assigned by the robot to each.

Disclosed herein is a novel and computationally efficient method of very robustly determining fruit ripeness within an image. The method will be described with reference to the flowchart indicated generally at 700 in FIG. 7. In the first step of the scheme (act 705) an image of a scene including agricultural produce is obtained, for example, via a camera or cameras affixed to or otherwise associated with an agricultural robot or other form of fruit object detector. In act 710 a cropped region of the original image which is the same size or slightly larger or smaller than the target fruit for which ripeness will be calculated is selected. The cropped region may be identified by a machine vision system programmed to identify the agricultural product or fruit in the image. The machine vision system may include, for example, a convolutional neural network that has been trained to identify individual items of agricultural product or fruit in an image. The machine vision system may indicate the identified produce by drawing a box around individual pieces of produce in an augmented reality image of the scene, for example, as illustrated in FIG. 5, discussed in further detail below.

Figure 3A:
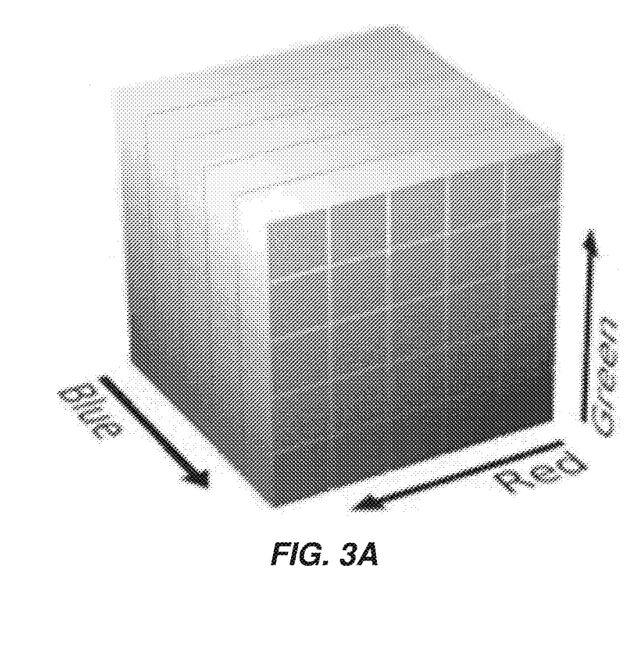
FIG. 3A illustrates a red-green-blue (RGB) color space.
Figure 3B:
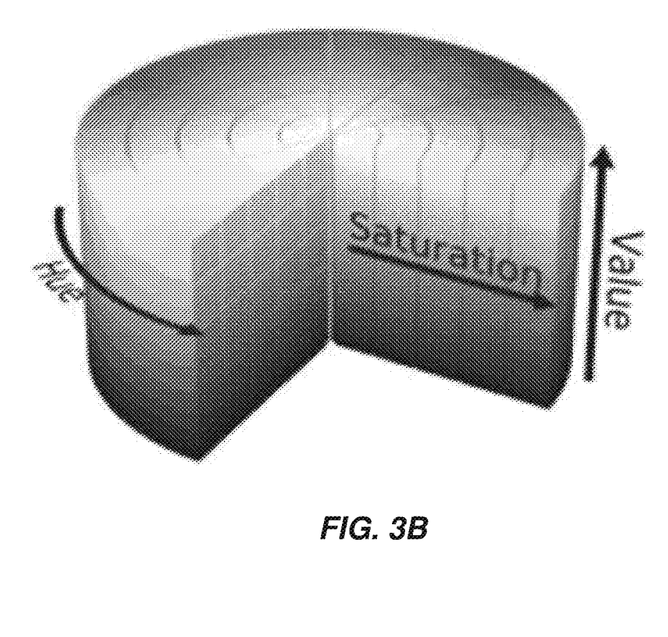
FIG. 3B illustrates a hue-saturation-value (HSV) color space.
Figure 4:
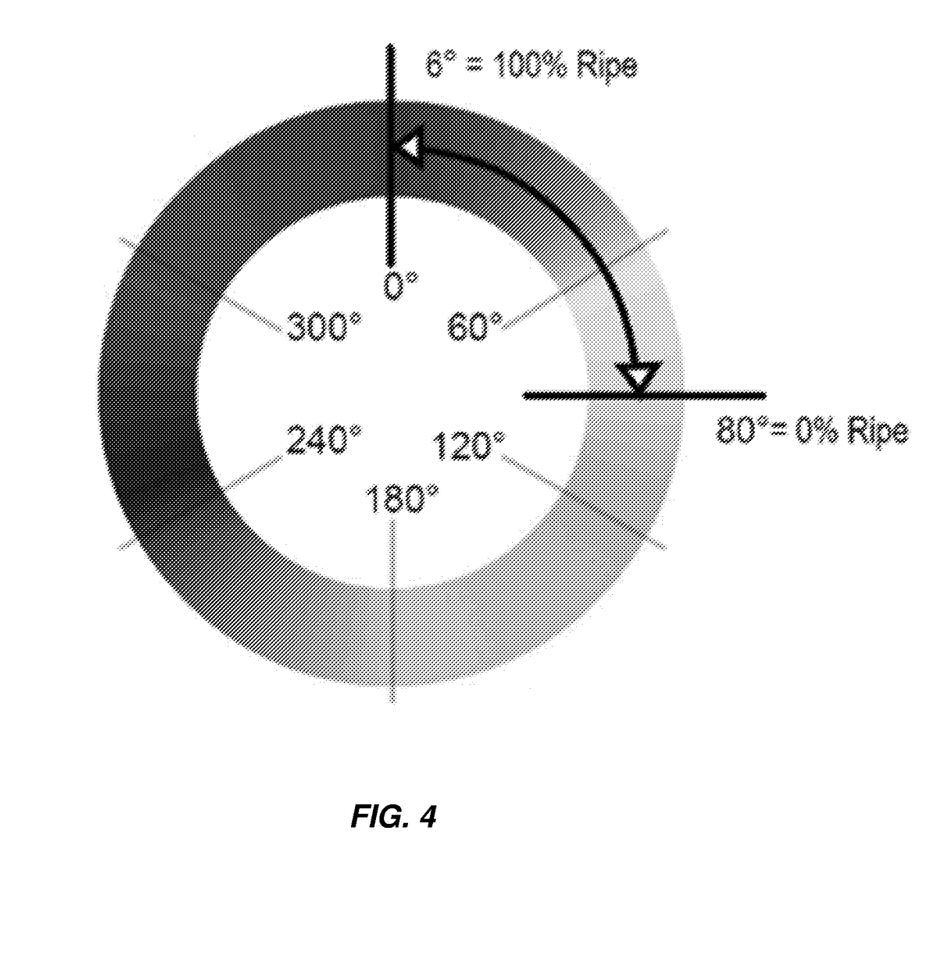
FIG. 4 illustrates a correlation between hue value and degree of ripeness for certain agricultural produce.

Typically, camera imaging sensors produce images in three channel RGB (red, green, and blue) color space (FIG. 3A). However, another encoding of this space is called HSV (hue, saturation, and value). In this space, colors are represented by their hue as an angle from 0-360 degrees about a color wheel (FIG. 3B) and their saturation (the intensity of the color) and value (the brightness of the color). This space is popular for color manipulation, since radiometric differences within a scene (like a surface texture or specular reflection) may change the color values of a pixel in RGB color space very easily whereas in HSV color space each pixel would have nearly the same hue. In act 715 of this embodiment's ripeness calculation strategy, the previously selected cropped image region is converted to HSV color representation from the original RGB using any method known in the art.

It is assumed that the object detector which identified this region accurately selects a region at exactly the physical extents of an individual item of produce for which the ripeness may be calculated. Since produce such as fruits are most often highly convex and uniform in shape (i.e., tomatoes are spheres or slightly eccentric ellipses, bell peppers have a slightly elongated and trapezoidal shape, cucumbers are highly eccentric ellipses or "slots" that hang vertically) it can be assumed that for a rectangular image region sized to the physical extents of the target item of produce greater than 50% of the pixels within that rectangular region will belong to the target item of produce. In empirical testing this assertion has proven true in the vast majority of cases and is sufficiently accurate for commercial applications.

However, in many cases an overlapping between objects will occur, and some level of occlusion may "cover" the target item of produce by another item of produce, leaf, or vine. To circumvent this, a specific training strategy may be employed when separately training a fully convolutional network or FCN to perform the object detection and bounding task. When annotating images which will be used to train that fruit object detection FCN, a strict rule is maintained not to annotate (or label with a manually placed bounding box at the object's extents) any object which is more than 50% occluded by other items of produce or materials. The resulting FCN automatically optimizes to exclude these cases and tends not to identify them as positively detected items of produce.

FIG. 5 illustrates examples of actual regions of interest (bounding boxes) automatically identified for individual fruits by a FCN in accordance with embodiments disclosed herein along with the final results of their ripeness calculation (and a small reticule indicating the corresponding hue value).

Given this strategy, we can now safely assume that since the region is set at the physical extents of an individual item of produce, that produce, due to its convex shape occupies more than 50% of the region by area, and the item of produce is less than 50% covered by other items of produce, and that a plurality of pixels in that region will reside on the image of the target item of produce. Having determined this through experiment, the next step in the ripeness approach technique (act 720 in FIG. 7) is to compute a histogram of the pixel population by hue and saturation (as shown on the right sides of FIGS. 6A and 6B scaled to 0-255 bits from 0-360 degrees around the hue wheel). Computing the histogram may include calculating the number of pixels at each of a range of discrete hue and saturation buckets.

Figure 6A:
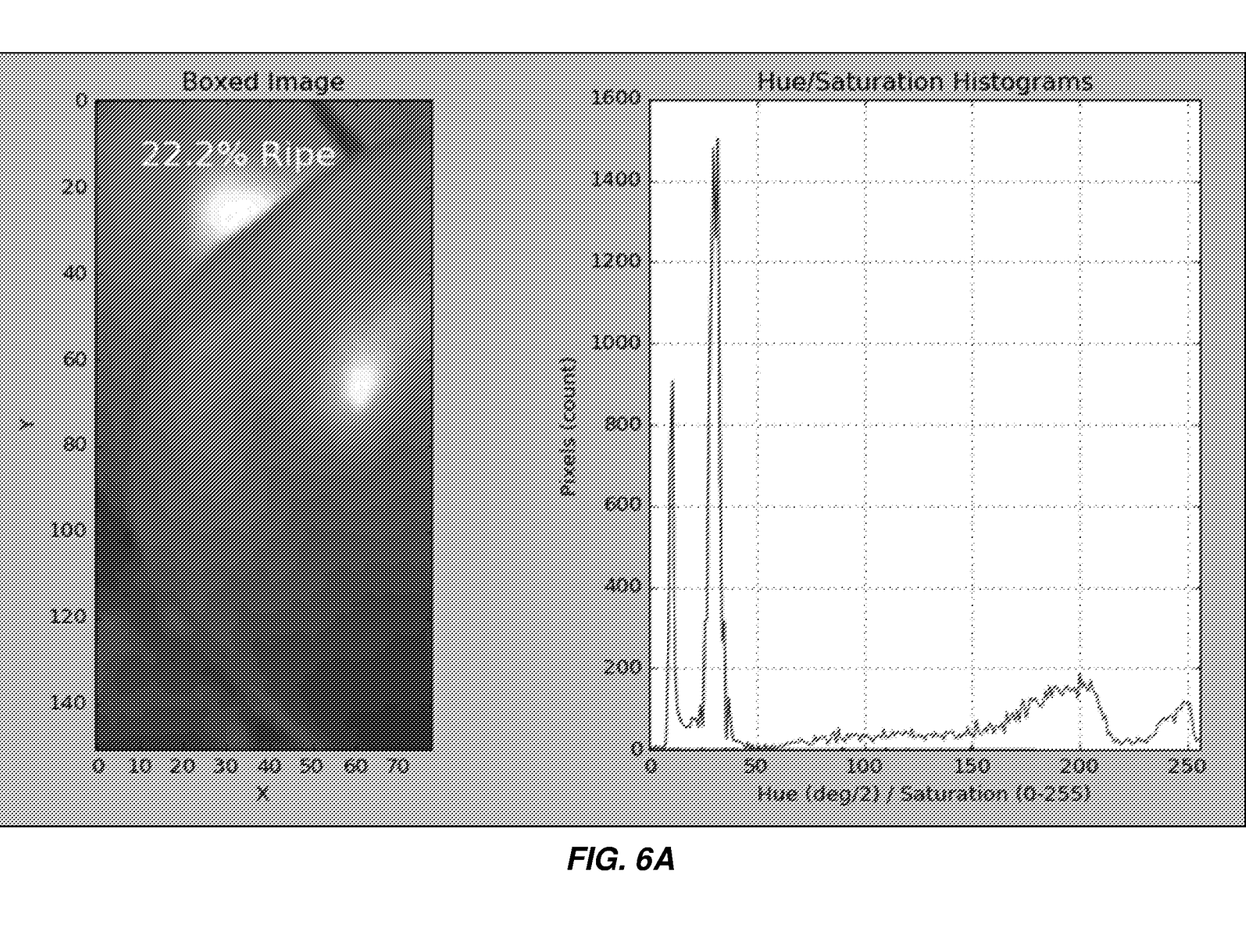
FIG. 6A illustrates an image of a tomato and a hue histogram used to determine the ripeness level of same.
Figure 6B:
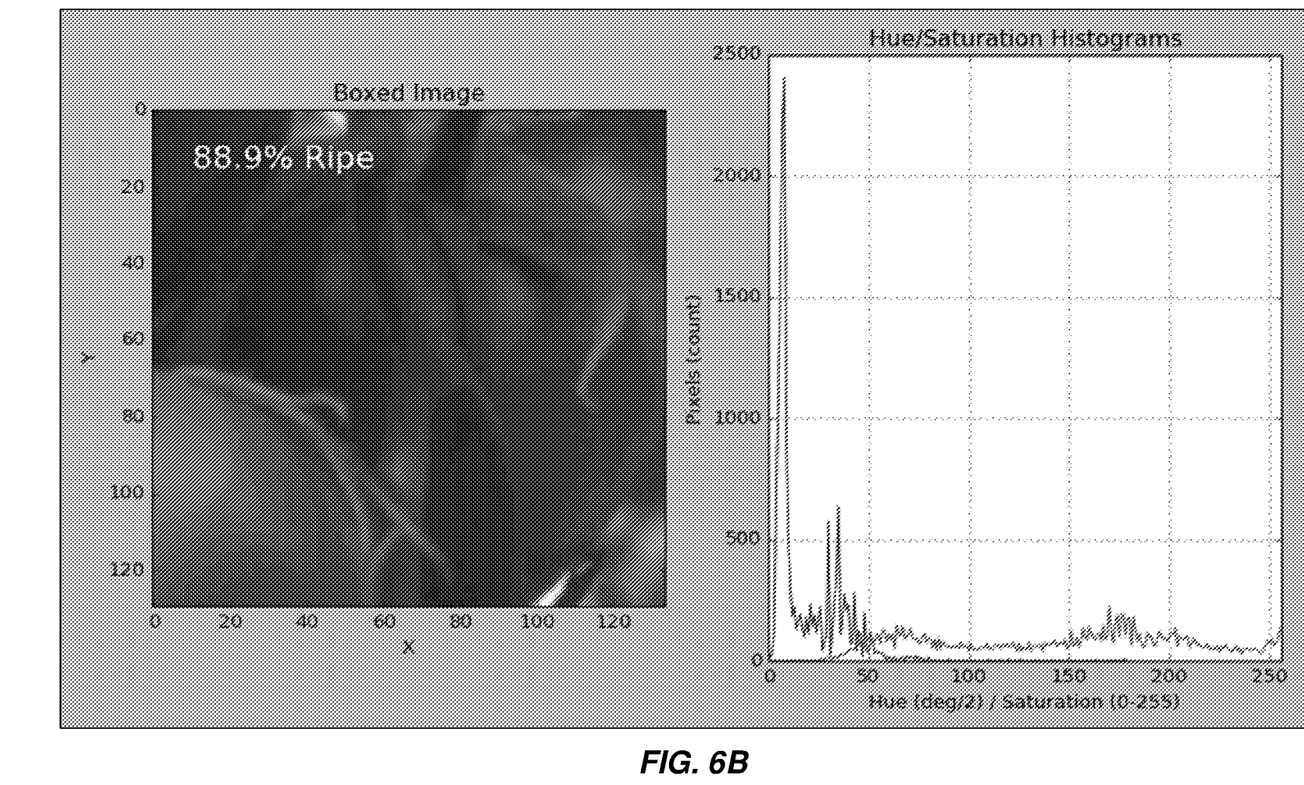
FIG. 6B illustrates an image of another tomato and a hue histogram used to determine the ripeness level of same.

Shown in FIGS. 6A and 6B are two sample outputs of the cropped image region of interest (left sides of FIGS. 6A and 6B) and the corresponding pixel population histogram by hue (histograms on leftmost sides) and saturation (histograms extending to right sides). It was discovered in this process that when properly exposed RGB images of most ripening produce (especially tomatoes and bell peppers) are processed via this technique, clear peaks (or maxima) in the hue histogram are visible, the center point of which correspond exactly to the ripeness of the produce on a proportional scale in hue that can be measured a priori and calibrated for each varietal of produce (in the case of the examples shown, the tomatoes are fully ripe at a hue value of 6 degrees and fully unripe or immature at a hue value of 80 degrees). Hue values between that which corresponds to fully ripe and that which corresponds to fully immature are then linearly interpolated to an overall ripeness percentage.

Figure 7:
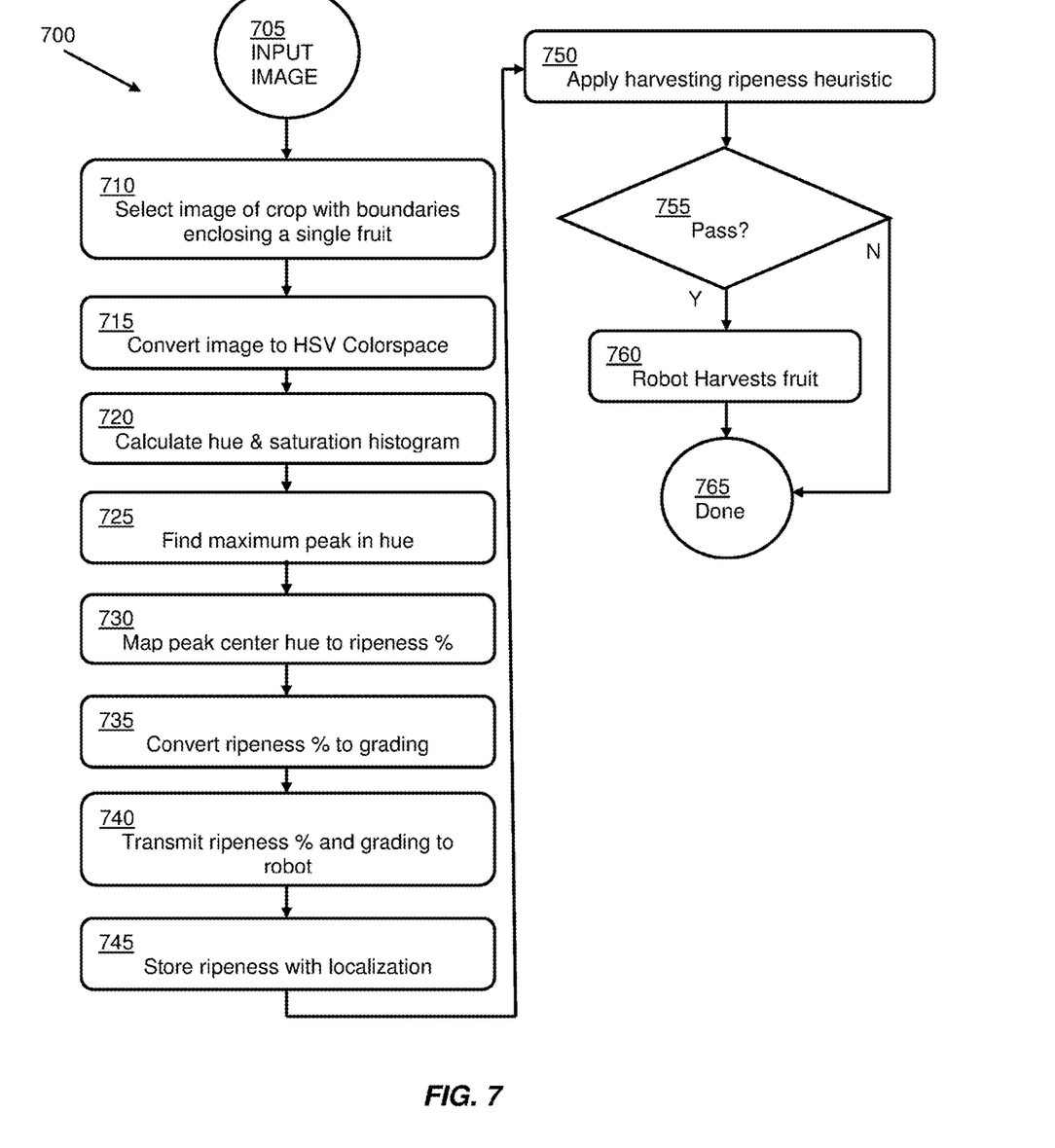
FIG. 7 is a flowchart of a method for determining ripeness of an agricultural product.

In accordance with the above, in act 725 of the method of FIG. 7, the maximum peak in the hue histogram is determined by, for example, finding the peak which corresponds to the largest pixel population in hue. In act 730 a ripeness % for an identified item of produce is determined from the location of the center of the peak in the hue histogram for that item of produce. An empirically determined lookup table or fitting function may be used to map hue to ripeness percentage, where ripeness is expressed as a percentage from 0% (wholly unripe) to 100% (fully ripe).

By design, this technique is highly robust to skewed results due to other partial occluding produce. An excellent example of this is shown in FIG. 6A, where a significant portion of an ripe tomato that is not the intended target is visible in the region of interest. This unwanted tomato appears in the histogram as a lesser magnitude second maxima, automatically discarded when determining the center hue value of the largest peak. Conveniently, this same hue histogram could be viewed and analyzed as a spectrum instead, where each dominant peak corresponds to a different item of produce at a different and unique ripeness level and where the magnitude of the corresponding peak indicates the relative area of that item of produce in the region of interest. Again, due to the assumptions established at the beginning of this section, we can assume with a very high degree of certitude (over 98% in empirical tests) that the dominant peak corresponds accurately to the ripeness of the intended target item of produce.

It should be noted that while in this case a "naïve" peak finding method in which the histogram global maximum is taken as the dominant peak center point is used, many alternate and well understood methods of "peak finding" within a spectrum (which the histogram resembles) can be employed to more accurately locate the center hue value of the dominant peak with better immunity to minor variations or noise. Other peak finding techniques could also be used to isolate additional partial items of produce visible in the region at other ripeness, if that information is of value for collection.

This overall scheme for calculating ripeness has proven to be very robust in field testing to date and has been confirmed by agricultural professionals to assign ripeness percentages that meet or exceed the accuracy of their manual grading scales. While ripenesses of tomatoes are estimated in the provided examples, the method can be extended to many different varieties of ripening produce. This method is also highly computationally efficient and can be conducted on high resolution images in less than five milliseconds using standard computers.

In act 735 of the method of FIG. 7, the ripeness % of a piece of produce may be converted to a ripeness grade. In some implementations, grower rules for ripeness grading may be used to convert ripeness % to grade class, for example, to one of five or six grades of ripeness. In some implementations the ripeness grade may be an easier parameter to work with to determine if a piece of produce is ready for harvesting than the calculated ripeness %.

In act 740, the ripeness % and/or ripeness grade may be transmitted to an agricultural robot configured to harvest the item of produce. The robotic system may store the measured ripeness values along with an indication of a location of the piece of produce obtained through analysis of the image including the piece of produce in a local database (act 745), for example, for later analysis after corresponding information for other pieces of produce in the same location are obtained.

In act 750 a harvesting ripeness heuristic is applied in which the robotic system or associated computer system uses a heuristic function in which the ripeness grade and/or ripeness % are considered to determine which items of produce are ready for harvesting.

In act 755 a decision is made by the agricultural robot or associated computer system whether a particular item of produce passes the harvesting ripeness heuristic test. If so, the agricultural robot harvests the item of produce (act 760). If the particular item of produce does not pass the harvesting ripeness heuristic test, either a decision is made whether another piece of produce is to be harvested, or the method ends (act 765).

Example System

Figure 8:
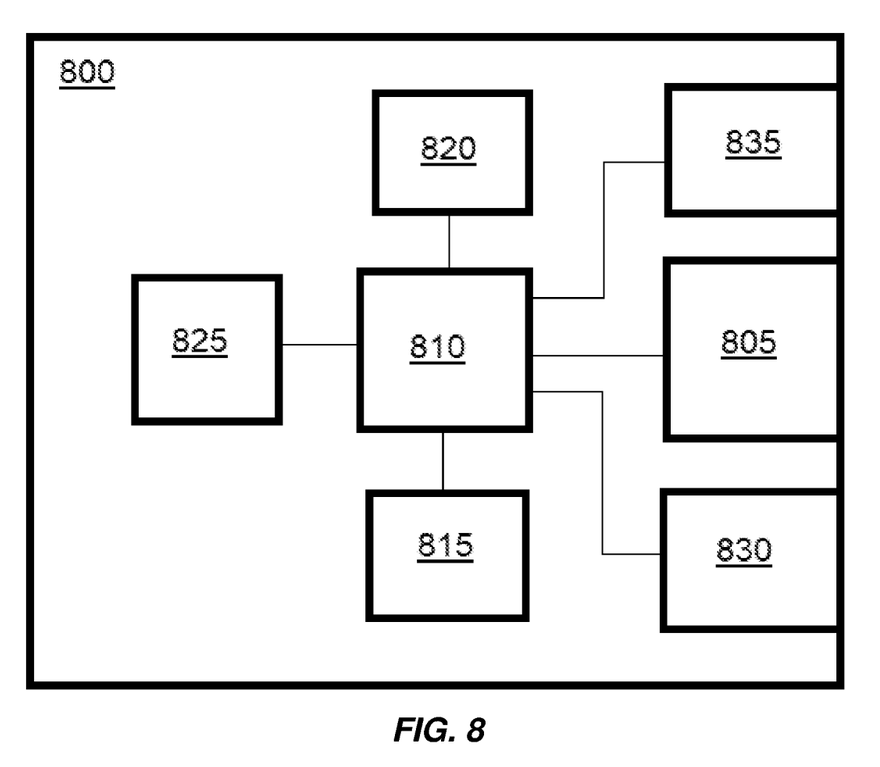
FIG. 8 is a schematic diagram of an example of a system for performing embodiments of the methods disclosed herein.

An example of a system for performing aspects and embodiments of the methods disclosed herein, e.g., for estimating ripeness of produce, is illustrated schematically in FIG. 8. The system 800 includes an image sensor 805 configured to measure intensities of light reflected from the produce at different frequencies and a processor 810 configured to determining a degree of ripeness of the produce from relative intensities of the light reflected from the produce at the different frequencies. The processor may be, for example, a commercially available processor such as the well-known Pentium™ or Core™ class processors available from the Intel Corporation or a special purpose application-specific integrated circuit (ASIC). The system 800 includes a memory 815, for example, a hard drive or solid state memory for storing programming instructions for the processor 810 or to store captured images or image data. The system 800 also includes one or more input devices 820, for example, a keyboard, mouse, trackball, microphone, touch screen, electrical connector or wireless modem for receiving programming instructions, and one or more output devices 825, for example, a printing device, display screen, speaker, or electrical connector or wireless modem for outputting data to an external system. Further included in the system 800 are a projector 830 configured to illuminate the produce with light in a bandwidth, for example, green light, that is reflected from the produce to a degree that varies with ripeness of the produce, and a light intensity meter 835 configured to measure an intensity of the light reflected from the produce. In some embodiments, the image sensor 805 and light intensity meter 835 may be combined as a single sensor.

Figure 9:
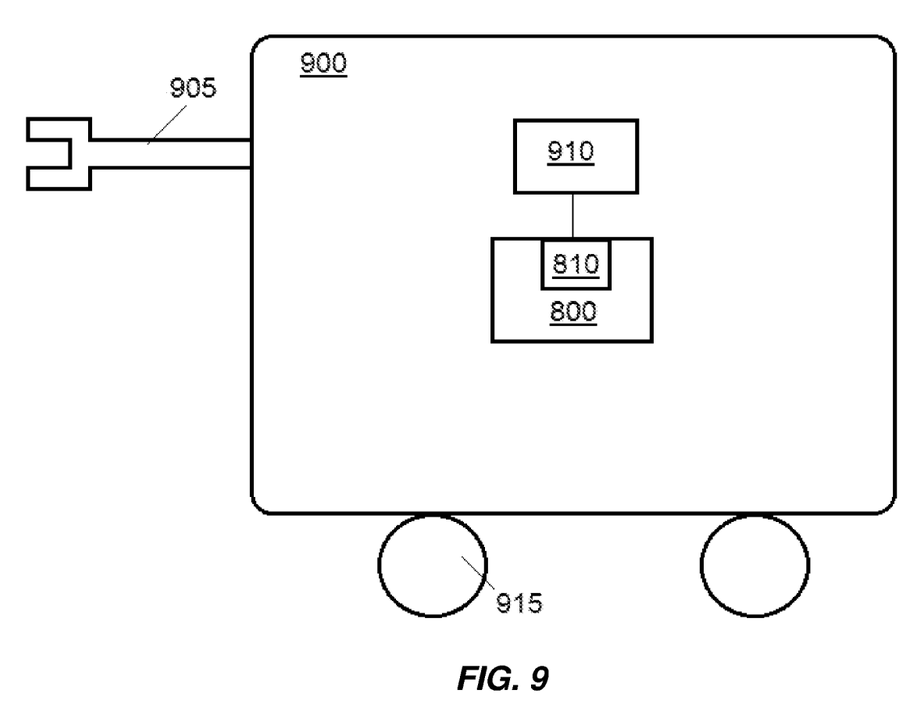
FIG. 9 illustrates an example of a robotic harvester.

The system 800 may be included in a robotic harvester 900, illustrated schematically in FIG. 9. The robotic harvester may include its own processor 910 in communication with the processor 810 of the system 800 or may be in communication with and operated by the processor 810. The harvester 900 may be configured to harvest items of agricultural produce identified by the system 800 as sufficiently ripe for harvesting using, for example, a robotic arm 905. The robotic harvester 900 may include wheels 915 or tracks or other forms of motive devices to move throughout an environment a harvest produce from different plants in the environment.

Having thus described several aspects of at least one implementation, it is to be appreciated various alterations, modifications, and improvements will readily occur to those skilled in the art. Such alterations, modifications, and improvements are intended to be part of this disclosure, and are intended to be within the spirit and scope of the disclosure. The acts of methods disclosed herein may be performed in alternate orders than illustrated, and one or more acts may be omitted, substituted, or added. One or more features of any one example disclosed herein may be combined with or substituted for one or more features of any other example disclosed. Accordingly, the foregoing description and drawings are by way of example only.

The phraseology and terminology used herein is for the purpose of description and should not be regarded as limiting. As used herein, the term "plurality" refers to two or more items or components. As used herein, dimensions which are described as being "substantially similar" should be considered to be within about 25% of one another. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method for estimating ripeness of produce, the method comprising:
   illuminating the produce with light;
   measuring intensities of the light reflected from the produce at different frequencies;
   selecting, by a convolutional neural network, a cropped region of an image of the produce, wherein the cropped region of the image of the produce is selected such that an image of a target item of produce within the cropped region of the image of the produce occupies more than 50% of the cropped region by an area and such that the target item of produce is less than 50% occluded by an object within the cropped region of the image of the produce;
   converting the cropped region of the image to a hue, saturation, and value (HSV) color representation;
   constructing a hue histogram of hues in the cropped region of the image; and
   determining a degree of ripeness of the target item of produce from both the intensities of the light reflected from the produce at the different frequencies and a dominant peak in the hue histogram.

2. The method of claim 1, wherein the cropped region is a same size as the target item of produce for which ripeness is to be calculated.

3. The method of claim 1, further comprising computing a histogram of pixel population of the cropped region of the image by hue and saturation.

4. The method of claim 1, further comprising identifying the dominant peak in the hue histogram.

5. The method of claim 4, further comprising determining the degree of ripeness of the target item of produce from a location of the dominant peak in the hue histogram.

6. The method of claim 5, further comprising calibrating a hue histogram peak location versus produce ripeness scale for different varieties of produce.

7. The method of claim 1, wherein the method is utilized to estimate ripeness of produce which exhibits a change in concentration of one or more of ß-carotene, lutein, lycopene, or other carotenoids as the produce ripens.

8. The method of claim 7, wherein the method is utilized to estimate ripeness of produce selected from the group consisting of tomatoes, peppers, and cucumbers.

9. The method of claim 1, further comprising providing an indication of whether the produce is sufficiently ripe for harvesting based on determination of the degree of ripeness of the produce.

10. The method of claim 9, further comprising communicating the indication of whether the produce is sufficiently ripe for harvesting to a robotic system configured to harvest the produce.

11. The method of claim 10, further comprising harvesting produce with the robotic system responsive to the produce being sufficiently ripe for harvesting.

12. A method for estimating ripeness of produce in an indoor agricultural environment having an ambient light power spectrum that differs from a power spectrum of natural outdoor light, the method comprising:
   illuminating the produce with light in a bandwidth that is reflected from the produce to a degree that varies with ripeness of the produce;
   measuring an intensity of the light reflected from the produce;
   selecting, by a convolutional neural network, a cropped region of an image of the produce, wherein the cropped region of the image of the produce is selected such that an image of a target item of produce within the cropped region of the image of the produce occupies more than 50% of the cropped region by an area and such that the target item of produce is less than 50% occluded by an object within the cropped region of the image of the produce;
   converting the cropped region of the image to a hue, saturation, and value (HSV) color representation;
   constructing a hue histogram of hues in the cropped region of the image; and
   determining a degree of ripeness of the target item of produce from both the intensity of the light reflected from the produce and a dominant peak in the hue histogram.

13. A system for estimating ripeness of produce, the system comprising:
   an image sensor configured to measure intensities of light reflected from the produce at different frequencies; and
   a processor configured to:
      receive, from a convolutional neural network, a cropped region of an image of the produce, wherein the cropped region of the image of the produce is selected such that an image of a target item of produce within the cropped region of the image of the produce occupies more than at least 50% of the cropped region by an area and such that the target item of produce is less than 50% occluded by an object within the cropped region of the image of the produce;
      convert the cropped region of the image to a hue, saturation, and value (HSV) color representation;
      construct a hue histogram of hues in the cropped region of the image; and
      determine a degree of ripeness of the target item of produce from both relative intensities of the light reflected from the produce at the different frequencies and a dominant peak in the hue histogram.

14. The system of claim 13, wherein the cropped region is a same size as the target item of produce for which ripeness is to be calculated.

15. The system of claim 14, wherein the processor is further configured to select the cropped region of the image such that greater than 50% of pixels in the cropped region of the image are included in an image of the target item of produce.

16. The system of claim 13, wherein the processor is further configured to compute a histogram of pixel population of the cropped region of the image by hue and saturation.

17. The system of claim 13, wherein the processor is further configured to identify the dominant peak in the hue histogram.

18. The system of claim 17, wherein the processor is further configured to determine the degree of ripeness of the target item of produce from a location of the dominant peak in the hue histogram.

19. The system of claim 18, further comprising a robotic harvester in communication with the processor and configured to harvest the target item of produce.

20. The system of claim 13, wherein the processor is further configured to provide an indication of whether the produce is sufficiently ripe for harvesting responsive to determining the degree of ripeness of the produce.

21. The system of claim 20, wherein the processor is further configured to communicate the indication of whether the produce is sufficiently ripe for harvesting to a robotic system configured to harvest the produce.

22. The system of claim 21, further comprising the robotic system configured to harvest the produce.

23. A robotic harvester configured to harvest items of agricultural produce identified as sufficiently ripe for harvesting by the system of claim 17.

24. The system of claim 13, wherein the processor is further configured to calibrate a hue histogram peak location versus produce ripeness scale for different varieties of produce.

25. The system of claim 13, wherein the produce exhibits a change in concentration of one or more of ß-carotene, lutein, lycopene, or other carotenoids as the produce ripens, wherein the produce is selected from the group consisting of tomatoes, peppers, and cucumbers.

26. A system for estimating ripeness of produce in an indoor agricultural environment having an ambient light power spectrum that differs from a power spectrum of natural outdoor light, the system comprising:
   a projector configured to illuminate the produce with light in a bandwidth that is reflected from the produce to a degree that varies with ripeness of the produce;
   a light intensity meter configured to measure an intensity of the light reflected from the produce; and
   a processor configured to
      receive, from a convolutional neural network, a cropped region of an image of the produce, wherein the cropped region of the image of the produce is selected such that an image of a target item of produce within the cropped region of the image of the produce occupies more than 50% of the cropped region by an area and such that the target item of produce is less than 50% occluded by an object within the cropped region of the image of the produce,
convert the cropped region of the image to a hue, saturation, and value (HSV) color representation,
construct a hue histogram of hues in the cropped region of the image, and
determine a degree of ripeness of the target item of produce from both the intensity of the light reflected from the produce and a dominant peak in the hue histogram.

* * * * *